United States Patent [19]

Albrecht et al.

[11] 3,932,456

[45] Jan. 13, 1976

[54] BIS-BASIC ESTERS AND AMIDES OF CARBAZOLE

[75] Inventors: William L. Albrecht; Robert W. Fleming, both of Cincinnati, Ohio

[73] Assignee: Richardson-Merrell Inc., Wilton, Conn.

[22] Filed: June 16, 1969

[21] Appl. No.: 833,718

[52] U.S. Cl. ............................... 260/315; 424/274
[51] Int. Cl.² ...................................... C07D 209/88
[58] Field of Search ............ 260/315, 346.2, 329.3

[56] References Cited
UNITED STATES PATENTS 3,190,853 6/1965 Watson ............................... 260/47

OTHER PUBLICATIONS

Burtner, et al., J.A.C.S. 62: 527–532 (3–40).

*Primary Examiner*—Henry R. Jiles
*Assistant Examiner*—C. M. S. Jaisle
*Attorney, Agent, or Firm*—George W. Rauchfuss, Jr.

[57] ABSTRACT

Novel bis-basic esters and amides of carbazole of the formula

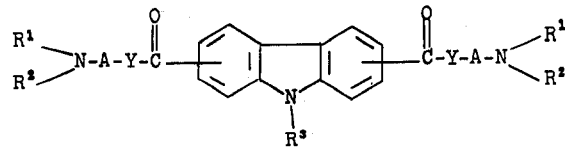

wherein:

A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or $R^1$ and $R^2$ taken together with the nitrogen atom to which they are attached is pyrrolidino, piperidino, N-(lower) alkylpiperazino, or morpholino;

B. each A is alkylene of 2 to about 8 carbon atoms and separates its adjacent Y and amino nitrogen by an alkylene chain of at least 2 carbon atoms;

C. each Y is oxygen, or N—R wherein R is hydrogen, methyl or ethyl; and

D. $R^3$ is hydrogen or (lower) primary or secondary alkyl; or a pharmaceutically acceptable acid addition salt thereof. These compounds can be used as pharmaceuticals for preventing or inhibiting a viral infection.

15 Claims, No Drawings

BIS-BASIC ESTERS AND AMIDES OF CARBAZOLE

This invention relates to novel bis-basic esters and amides of carbazole, their method of preparation and use as antiviral agents.

The preparation of carbazole-3,6-dicarboxylic acid and 9-ethylcarbazole-3,6-dicarboxylic acid has been reported by Y. Nagai and C. C. Huang, Bull. Chem. Soc. Japan, 38, 951 (1965), H. Gilman and S. M. Spatz, J. Am. Chem. Soc., 63, 1553 (1941) and R. W. G. Preston, S. H. Tucker and J. M. L. Cameron, J. Chem. Soc., 500 (1942). However, to applicants' knowledge, the bis-basic substituted esters or amides of carbazole are novel compounds.

The compounds of this invention include both the base form and pharmaceutically acceptable acid addition salts of the base form wherein the base form can be represented by the formula

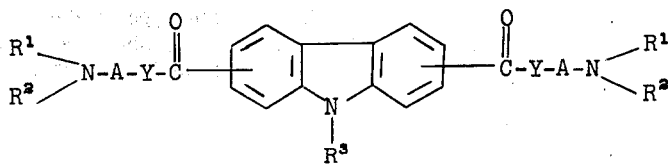   Formula I wherein:
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent Y and amino nitrogen by an alkylene chain of at least 2 carbon atoms;
C. each Y is oxygen, or N-R wherein R is hydrogen, methyl or ethyl; and
D. $R^3$ is hydrogen or (lower) primary or secondary alkyl; or a pharmaceutically acceptable acid addition salt thereof.

It can be seen from the above Formula I that one of the side chains, that is,

can be linked to the carbazole ring by replacement of any of the four hydrogens of one of the benzenoid rings, and similarly, the second side chain is attached to the second benzenoid ring. Thus, one of the side chains can be in any of the positions of 1 through 4 of the carbazole ring and the other can be in any of the positions 5 through 8. Illustratively, the carbazole ring can be substituted in positions 1,8; 2,6; or 3,6. Preferably, the carbazole ring carries the side chains in the 3,6-positions.

Each of the alkylene groups as represented by "A" in the above generic Formula I is an alkylene group having from 2 to about 8 carbon atoms which can be straight chained or branched chained and which separates its adjacent Y from the amino nitrogen by an alkylene chain of at least two carbon atoms, i.e., the Y grouping and the amino nitrogen are not on the same carbon atom of the alkylene group. Each of the alkylene groups as represented by A can be the same or different. Preferably both of these groups are the same. Illustrative of alkylene groups as represented by A there can be mentioned: 1,2-ethylene; 1,3-propylene; 1,4-butylene; 1,5-pentylene; 1,6-hexylene; 2-methyl-1,4-butylene; 2-ethyl-1,4-butylene; 3-methyl-1,5-pentylene and the like. Preferably, A is alkylene having from 3 to 6 carbon atoms.

Each amino group, i.e.,

of Formula I, can be a primary, secondary or tertiary amino group. Each of $R^1$ and $R^2$ can be hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is a saturated monocyclic heterocyclic group.

Illustrative of cycloalkyl groups as represented by each of $R^1$ and $R^2$ there can be mentioned: cyclopropyl; cyclobutyl; cyclopentyl; cyclohexyl; and the like. When $R^1$ or $R^2$ represent alkenyl groups, the vinyl unsaturation is in other than the 1-position of said alkenyl group. Illustrative of alkenyl groups as can be represented by each of $R^1$ and $R^2$ there can be mentioned: allyl; 3-butenyl; 4-hexenyl; and the like. Illustrative of heterocyclic groups represented by $R^1$ and $R^2$, together with the nitrogen atom to which they are attached, there can be mentioned various saturated monocyclic heterocyclic groups such as those generally equivalent to di(lower)alkylamino groups in the pharmaceutical arts, e.g., pyrrolidino, piperidino, morpholino, N-(lower)alkylpiperazino such as N-methylpiperazino; N-ethylpiperazino; and the like. Each of the $R^1$ and $R^2$ groups can be the same or different. Preferably all of the $R^1$ and $R^2$ groups are the same. The amino groups are preferably tertiary amino groups such as di(lower)alkylamino, dialkenylamino or each set of $R^1$ and $R^2$ together with the nitrogen to which they are attached is pyrrolidino, piperidino, N-(lower)-alkylpiperazino or morpholino.

The $R^3$ group in Formula I can be hydrogen or (lower) primary or secondary alkyl. Preferably $R^3$ is (lower) primary or secondary alkyl. Each Y group in Formula I can be oxygen or N-R wherein R is hydrogen, methyl or ethyl. Preferably, R is hydrogen.

The term (lower)alkyl or (lower)alkoxy as used herein relates to such groups having from 1 to 6 carbon atoms. $R^1$ and $R^2$ may be methyl, ethyl, n-propyl, isopropyl, n-butyl, secondary butyl, tertiary butyl, isoamyl, n-pentyl, n-hexyl, and the like; and $R^3$ may be methyl, ethyl, n-propyl, isopropyl, n-butyl, secondary butyl, isoamyl, n-pentyl, and the like.

Illustrative of the carbazole compounds of this invention are: bis(3-diethylaminopropyl) 9-ethylcarbazole-3,6-dicarboxylate; bis(3-diethylaminopropyl) carbazole-3,6-dicarboxylate; bis(3-dibutylaminopropyl) 9-methylcarbazole-3,6-dicarboxylate; bis(3-piperidinopropyl) 9-ethylcarbazole-3,6-dicarboxylate; bis(2-diethylaminoethyl) 9-ethylcarbazole-3,6-dicarboxylate; bis(4-diethylaminobutyl) carbazole-3,6-dicarboxylate; bis(3-diethylaminopropyl) 9-(2-methylpropyl)-carbazole-3,6-dicarboxylate; bis(5-dipropylaminopentyl) carbazole-3,6-dicarboxylate; bis[2-(N-methyl-4-piperidyl)-ethyl]-9-methylcarbazole-3,6-dicarboxylate; bis(3-diethylaminopropyl) carbazole-2,6-dicarboxylate; bis(3-diethylaminopropyl) 9-methylcarbazole-1,8-dicarboxylate; bis(3-diethylaminopropyl) 9-n-butylcarbazole-3,6-dicarboxylate; N,N'-bis(3-dibutylaminopropyl) 9-ethylcarbazole-3,6-dicarboxamide; N,N'-diethyl-N,N'-bis(2-diethylaminoethyl) 9-ethylcarbazole-3,6-dicarboxamide.

It can be seen from the generic Formula I and its description that the compounds of this invention can be (a) carbazole esters or (b) carbazole amides, which can be illustrated by the following formulas, respectively:

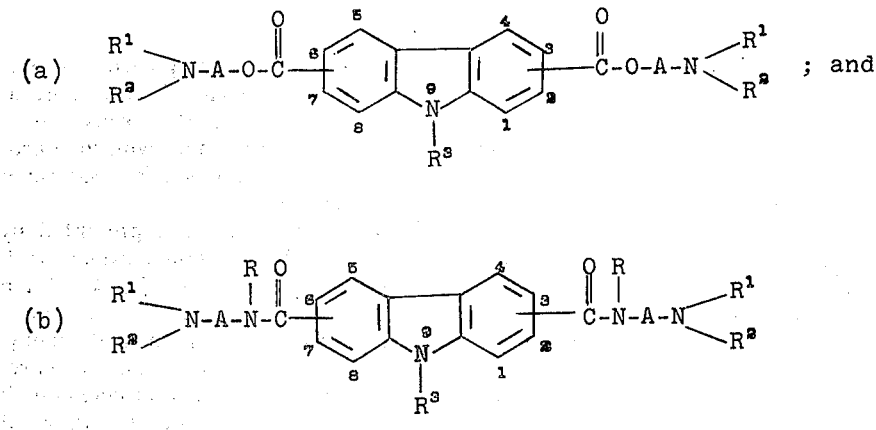

wherein R, $R^1$, $R^2$, $R^3$ and A have the same meaning as that in Formula I.

Salts of the base compounds of this invention are primarily pharmaceutically acceptable acid addition salts with inorganic or organic acids. Illustrative of such acids are: hydrochloric; hydrobromic; sulfuric; lactic; malonic; maleic; and citric acids. Mono- or di-acid salts may be formed; also, the salts can be hydrated, e.g., monohydrate, or substantially anhydrous.

The compounds of this invention, also simply referred to as active ingredients, can be administered to animals, such as warm-blooded animals and particularly mammals, for their prophylactic or therapeutic antiviral effects by conventional modes of administration, either alone, but preferably with pharmaceutical carriers. Illustratively, administration can be parenterally, e.g., subcutaneously, intravenously, intramuscularly or intraperitoneally, or topically, e.g., intranasally or intravaginally. Alternatively or concurrently, administration can be by the oral route.

The dosage administered will be dependent upon the virus for which treatment or prophylaxis is desired, the type of animal involved, its age, health, weight, extent of infection, kind of concurrent treatment, if any, frequency of treatment and the nature of the effect desired. Illustratively, dosage levels of the administered active ingredients can be: intravenously, 0.1 to about 10 mg/kg; intraperitoneal, 0.1 to about 50 mg/kg; subcutaneous, 0.1 to about 250 mg/kg; orally, 0.1 to about 500 mg/kg and preferably about 1 to 250 mg/kg; intranasal instillation, 0.1 to about 10 mg/kg; and aerosol, 0.1 to about 10 mg/kg of animal (body) weight.

The active ingredients, together with pharmaceutical carriers, can be employed in unit dosage forms such as solids, e.g., tablets, capsules, powder packets, or liquid solutions, suspensions, or elixirs for oral administration and ingestion or liquid solutions for parenteral use. The quantity of active ingredient in the dosage will generally differ depending on the type of unit dosage, the type of animal, and its weight. Thus, each unit dosage can contain from about 1 milligram (mg) to about 30 grams of active ingredient and preferably from about 25 to 5000 mg. of active ingredient in a pharmaceutical carrier.

The solid unit dosage forms can be of the conventional type. Thus, the solid carrier can be a capsule which can be of the ordinary gelatin type. In the capsule there can be from about 10 to about 90% by weight of active ingredient and from 90 to 10% of a carrier, e.g., lubricant and inert fillers such as lactose, sucrose, corn starch, and the like. In another embodiment, the active ingredient is tabletted with conventional carriers, e.g., binders such as acacia, corn starch or gelatin, disintegrating agents such as corn starch, potato starch, or alginic acid, and a lubricant such as stearic acid, or magnesium stearate. In yet another embodiment, the active ingredient is put into powder packets and employed. These solid unit dosages will generally contain from about 5 to 95% of the active ingredient by weight of the unit dosage and preferably from about 20 to 90% by weight thereof. The solid unit dosage forms will generally contain from about 1 mg. to about 30 grams of the active ingredient and preferably from about 25 mg. to about 5000 mg. of the active ingredient.

The pharmaceutical carrier can, as previously indicated, be a sterile liquid such as water and oils, with or without the addition of a surfactant. Illustrative of oils there can be mentioned those of petroleum, animal, vegetable or synthetic origin, e.g., peanut oil, soybean oil, mineral oil, sesame oil, and the like. In general, water, saline, aqueous dextrose, and related sugar solutions and glycols such as propylene glycol or polyethylene glycol are preferred liquid carriers, particularly for injectable solutions. Sterile injectable solutions such as saline, e.g., isotonic saline, will ordinarily contain from about 0.5 to 25% and preferably from about 1 to 10% by weight of the active ingredient in the composition.

As mentioned above, oral administration can be in a suitable suspension or syrup, in which the active ingredient ordinarily will constitute from about 0.5 to 10%, and preferably from about 1 to 5%, by weight. The pharmaceutical carrier in such composition can be a watery vehicle such as an aromatic water, a syrup or a pharmaceutical mucilage; also, a suspending agent for viscosity control such as magnesium aluminum silicate, carboxymethylcellulose or the like as well as a buffer, preservative, etc.

The active ingredients can also be admixed in animal feed or incorporated into the animal's drinking water. For most purposes, an amount of active ingredient will be used to provide from about 0.0001 to 0.1% by weight of the active ingredient based on the total weight of feed intake. Preferably, from 0.001 to 0.02% by weight will be used. The selection of the particular feed is within the knowledge of the art and will depend, of course, on the animal, the economics, natural materials available, and the nature of the effect desired.

The active ingredients can be admixed in animal feed concentrates, suitable for preparation and sale to farmers or livestock growers for addition to the animal's feedstuffs in appropriate proportion. These concentrates can ordinarily comprise about 0.5 to about 95% by weight of the active ingredient compounded together with a finely divided solid, preferably flours, such as wheat, corn, soya bean and cottonseed. Depending on the recipient animal, the solid adjuvant can be ground cereal, charcoal, fuller's earth, oyster shell and the like. Finely divided attapulgite and bentonite can also be used.

For use as aerosols the active ingredients can be packaged in a pressurized aerosol container together with a gaseous or liquefied propellant, e.g., dichlorodifluoromethane, carbon dioxide, nitrogen, propane, etc. with the usual adjuvants such as co-solvents, and wetting agents, as may be necessary or desirable.

Inter alia, the active ingredients induce the formation of interferon when host cells are subjected to such ingredients, e.g., contact of an active ingredient with tissue culture or administration to animals. Thus, these active ingredients can be used as antiviral agents for inhibiting or preventing a variety of viral infections by administering such an ingredient to an infected animal, e.g., warm-blooded animal, such as a mammal, or to such animal prior to infection. Illustratively, the compounds can be administered to prevent or inhibit infections of: picornaviruses, e.g., encephalomyocarditis; myxoviruses, e.g., Influenza $A_0PR_8$; arboviruses, e.g., Semliki Forest; and poxviruses, e.g., Vaccinia, IHD. When administered prior to infection, i.e., propylactically, it is preferred that the administration be within 0 to 96 hours prior to infection of the animal with pathogenic virus. When administered therapeutically to inhibit an infection, it is preferred that the administration be within about a day or two after infection with pathogenic virus.

The compounds of this invention can be prepared by a variety of procedures including the following:

1.

A. The reaction of a carbazole dicarboxylic acid or a reactive derivative thereof such as an acid halide or ester of the formula

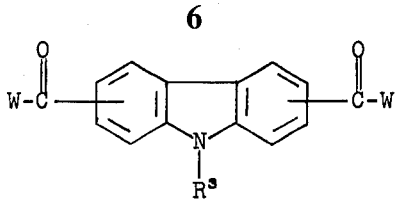

wherein $R^3$ is hydrogen or (lower) primary or secondary alkyl and W is hydroxy, halogen such as chlorine or bromine, or a (lower)alkoxy such as methoxy or ethoxy, with at least two equivalents of an aminoalkanol or aminoalkylamine of the formula

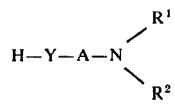

wherein Y is oxygen or N-R wherein R is hydrogen, methyl or ethyl, A is alkylene of 2 to about 8 carbon atoms, either straight chain or branched, and each $R^1$ and $R^2$ is as previously defined.

B. The esterification can be achieved by allowing the carbazole dicarboxylic acid, where W in the above formula is hydroxy, to react with at least two equivalents of the appropriate aminoalkanol in an inert solvent in the presence of a catalyst and employing general methods for removing water from the reaction site. Preferred solvents are chloroform, isopropanol, dioxane, toluene and the like. The reaction may be catalyzed by the use of mineral acids including hydrochloric, sulfuric or certain organic acids such as p-toluenesulfonic acid. Methods whereby water can be removed from the reaction include the use of water scavengers such as the carbodiimides or by the azeotropic removal of water. The reaction will proceed at temperatures ranging from 50°–150°C. over a period of 6 to 72 hours depending upon the solvent and catalyst.

C. Preferably, the esterification can be achieved by allowing the acid halide, where W in the above formula is halogen, to react with at least two equivalents of the appropriate aminoalkanol. The esters of this invention can be produced in a variety of inert solvents over a wide range of temperature and reaction time. The solvents of choice include chloroform, dioxane, tetrahydrofuran, and the aromatic solvents such as benzene and toluene. In chloroform, the reaction is generally complete within one hour at the reflux temperature of the solvent, although the reaction time can range from 15 minutes to 3 days. In like manner, the amides of this invention can be prepared by allowing the carbazole di-acid halide to react with at least two equivalents of the appropriate aminoalkylamine. The preferred reaction conditions are those which employ chloroform as the solvent and heating at the reflux temperature of said solvent for 3–18 hours.

D. The compounds of this invention may also be produced by a transesterification reaction in which a (lower)-alkoxy ester of the carbazole dicarboxylic acid, where W, for example, is methoxy or ethoxy in the above formula, is caused to react with at least two equivalents of the appropriate aminoalkanol under suitable conditions. This type of reaction is catalyzed by alkaline or acid catalysts and is reversible. The compounds of this invention may be produced by causing the equilibrium to be shifted by removing the lower alkanol component or by employing a large excess of the aminoalkanol. Preferably the reaction is carried out by removing the lower alkanol component with the use of an alkaline catalyst. The lower alkanol may be removed by direct distillation or distillation with a suitable solvent. Suitable alkaline catalysts are alkali metals, sodium or potassium; alkali lower alkoxides, such as sodium methoxide or sodium ethoxide; alkali amides such as lithium or sodium amide; etc. Suitable solvents are those forming an azeotropic distillation mixture with the lower alkanol, for example, benzene or toluene, or a solvent which boils sufficiently higher than the alkanol to permit removal of the alkanol by distillation at a temperature below that of the boiling range of the solvent. The amides of this invention may also be produced by allowing the lower alkoxy ester of the carbazole dicarboxyic acid to react with at least two equivalents of the appropriate aminoalkylamine under the conditions as for the esters.

2. The esters of this invention can be produced by allowing the carbazole dicarboxylic acid, or an activated salt thereof, to react with at least two equivalents of an aminoalkylhalide in a suitable organic solvent such as chloroform or isopropanol. The aminoalkyl portion of the reactant is the same as in 1-A above. The reaction conditions can vary from 6 hours to 72 hours over a temperature range of from room temperature to the reflux temperature of the solvent employed in the presence or absence of an activating moiety such as inorganic cations including sodium and silver or organic activators such as benzyltrimethylammonium chloride. These activators may be present in stoichiometric amounts or catalytic quantities. Since these activators considerably reduce the reaction time, the preferred conditions are to use a catalytic amount of benzyltrimethylammonium chloride and allow the reaction to proceed for 6–18 hours at the reflux temperature of isopropanol.

3. The compounds of this invention can be prepared by allowing a carbazole ω-haloalkyl diester or diamide, prepared by general methods, of the formula:

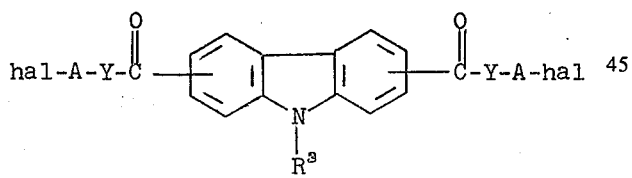

wherein $R^3$, Y and A are as previously defined and hal is chlorine, bromine or iodine to react with at least two equivalents of an amine of the formula:

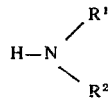

wherein $R^1$ and $R^2$ are as previously defined. The carbazole ω-haloalkyl diester or diamide may be prepared by the reaction of a carbazole dicarbonyl chloride with at least two equivalents of an ω-haloalkanol or an ω-haloalkylamine in a suitable solvent such as chloroform to give the respective products. The preferred halogen in the above formula is bromine or iodine. The reaction is conducted in the presence of stoichiometric amounts of a material which will effectively remove the acid generated in the course of the reaction. Suitable acid binding reagents are anhydrous sodium or potassium carbonate or extra equivalents of the amine. The solvents of choice are non-protonic organic liquids such as toluene, chloroform, diethyl ether and dioxane. Suitable conditions are those in which components are allowed to react in toluene at 25° to 100°C. for 24 hours to 72 hours in the presence of potassium carbonate. A pressure vessel may be required as higher temperatures are employed and/or low boiling amines are being reacted.

4. The secondary or primary amino derivatives of the esters of this invention can be prepared by the various procedures under 1 above, if the amino group of the aminoalkanol is suitably blocked to reactivity by formation of a salt or, preferably, by substituting it with a readily removable blocking group such as trifluoroacetyl, carbobenzoxy, or the like, followed by removal of the blocking group with a suitable technique such as mild acid hydrolysis or catalytic reduction.

The following examples are illustrative of the invention.

EXAMPLE 1

Preparation of bis(3-diethylaminopropyl) 9-ethylcarbazole-3,6-dicarboxylate dihydrochloride To 250 ml. of isopropanol was added 10.0 g. (0.035 mole) of 9-ethylcarbazole-3,6-dicarboxylic acid, 21.2 g. (0.14 mole) of 3-diethylaminopropylchloride and 0.5 ml. of 60% aqueous benzyltrimethylammonium chloride. The solution was heated at reflux for 2 hours with stirring and then allowed to stir overnight at room temperature. Addition of ether to the reaction mixture gave the crystalline product which was recrystallized twice from methanol-acetone, m.p. 233°–234°, $\lambda_{max}^{EtOH}$ 252, $E_{1\ cm}^{1\%}$ 865.

EXAMPLE 2

Preparation of bis(3-diethylaminopropyl) carbazole-3,6-dicarboxylate dihydrochloride hemihydrate To 250 ml. of isopropanol was added 10.5 g. (0.07 mole) of 3-diethylaminopropylchloride and 8.8 g. (0.035 mole) of carbazole-3,6-dicarboxylic acid and the mixture was heated at reflux for 2 hours. On cooling, the product crystallized and was collected by filtration, washed with ether, dried and dissolved in water. The aqueous solution was made basic with saturated sodium bicarbonate and the product was extracted with ether, the ether solution was washed with water, dried, and made acidic with ethereal hydrogen chloride. The solid product was crystallized twice from methanol-butanone, m.p. 230°–233°, $\lambda_{max}^{H_2O}$ 249, $E_{1\ cm}^{1\%}$ 885.

EXAMPLE 3

Preparation of N,N'-bis(3-dibutylaminopropyl) carbazole-3,6-dicarboxamide bis-dihydrogen citrate A solution of 0.03 mole of carbazole 3,6-dicarbonyl chloride and 0.06 mole of 3-dibutylaminopropylamine in 400 ml. of chloroform is heated at reflux for 4 hours. The chloroform solution is extracted with water and the aqueous layer made basic with saturated sodium bicarbonate solution. The free base is extracted with ether, washed with water, dried over anhydrous magnesium sulfate and concentrated in vacuo. The residue is dissolved in methanol and converted to the dihydrogen citrate salt by treating the methanol solution with two equivalents of citric acid. The product is crystallized from methanol-butanone.

EXAMPLE 4

Preparation of N,N'-bis(3-dibutylaminopropyl) 9-ethylcarbazole-3,6-dicarboxamide bis-dihydrogen citrate By the procedure of Example 3, one equivalent of 9-ethylcarbazole-3,6-dicarbonyl chloride is allowed to react with two equivalents of 3-dibutylaminopropylamine to give the product.

EXAMPLE 5

Preparation of bis(3-dibutylaminopropyl) 9-ethylcarbazole-3,6-dicarboxylate dihydrochloride By the procedure of Example 2, one equivalent of 9-ethylcarbazole-3,6-dicarboxylic acid is allowed to react with two equivalents of 3-dibutylaminopropyl-chloride in the presence of a catalytic amount of benzyltrimethylammonium chloride to give the product.

EXAMPLE 6

Preparation of bis(3-piperidinopropyl) 9-ethylcarbazole-3,6-dicarboxylate dihydrochloride By the procedure of Example 2, one equivalent of 9-ethylcarbazole-3,6-dicarboxylic acid is allowed to react with two equivalents of 3-piperidinopropyl chloride in the presence of a catalytic amount of benzyltrimethylammonium chloride to give the product.

EXAMPLE 7

Preparation of bis(3-dimethylaminopropyl) 9-ethylcarbazole-3,6-dicarboxylate dihydrochloride By the procedure of Example 2, one equivalent of 9-ethylcarbazole-3,6-dicarboxylic acid is allowed to react with two equivalents of 3-dimethylaminopropyl chloride in the presence of a catalytic amount of benzyltrimethylammonium chloride to give the product.

EXAMPLE 8

Preparation of bis(5-amino-2,2-dimethylpentyl) 9-ethylcarbazole-3,6-dicarboxylate dihydrochloride A solution of two molar equivalents of 5-amino-2,2-dimethyl-1-pentanol as the hydrochloride salt and one molar equivalent of 9-ethylcarbazole-3,9-dicarbonyl chloride in a sufficient volume of chloroform is refluxed for several hours. The product, bis(5-amino-2,2-dimethylpentyl) 9-ethylcarbazole-3,6-dicarboxylate dihydrochloride, can be purified by recrystallization from methanol-ethyl acetate.

EXAMPLE 9

Preparation of bis(5-ethylamino-2,2-dimethylpentyl) 9-ethylcarbazole-3,6-dicarboxylate dihydrochloride This secondary amine can be prepared by the procedure of Example 8 by employing the N-ethyl derivative of 5amino-2,2-dimethyl-1-pentanol.

EXAMPLE 10

Preparation of bis(3-diethylaminopropyl) 9-methylcarbazole-1,8-dicarboxylate

Bis(3-diethylaminopropyl) 9-methylcarbazole-1,8-dicarboxylate can be prepared by the esterification of 9-methylcarbazole 1,8-dicarboxylic acid, the synthesis of which is reported by H. Gilman and S. Spatz, J. Org. Chem. 17, 860 (1952), according to the procedure of Example 1.

EXAMPLE 11

Preparation of bis(3-diethylaminopropyl) carbazole 2,6-dicarboxylate

Bis(3-diethylaminopropyl) carbazole 2,6-dicarboxylate can be prepared by the esterification of carbazole-2,6-dicarboxylic acid, the synthesis of which is reported by D. Brooke and S. Plant, J. Chem. Soc., 2212 (1956), according to the procedure of Example 1.

EXAMPLE 12

This example illustrates antiviral activity of bis(3-diethylaminopropyl) 9-ethylcarbazole-3,6-dicarboxylate dihydrochloride.

Two groups of mice were inoculated with a fatal dose (12 $LD_{50}$) of encephalomyocarditis. Each mouse weighed from approximately 12 to 15 grams and each of the two groups of mice contained from 10 to 30 animals. The mice in one of the groups were treated both prophylactically and therapeutically by subcutaneous injections of bis(3-diethylaminopropyl) 9-ethylcarbazole-3,6-dicarboxylate dihydrochloride. The injections were given 28, 22 and 4 hours prior to inoculation with the virus and 2, 20 and 26 hours after inoculation. The volume of each injection was 0.25 ml. and contained the active compound at a dosage level of 50 mg. per kg. dissolved in sterile water which also contained 0.15% of hydroxyethyl-cellulose. The control animals received a sham dosage of the same volume of the vehicle which did not contain the active ingredient. Observations over a 10-day period showed that the treated group of mice survived for a longer time than the controls.

EXAMPLE 13

An illustrative composition for a parenteral injection is the following wherein the quantities are on a weight to volume basis.

| (a) | Bis(3-diethylaminopropyl) 9-ethylcarbazole-3,6-dicarboxylate dihydrochloride | 100 mg. |
|---|---|---|
| (b) | Sodium chloride | q.s. |
| (c) | Water for injection to make | 10 ml. |

The composition is prepared by dissolving the active ingredient and sufficient sodium chloride in water for injection to render the solution isotonic. The composition may be dispensed in a single ampule containing 100 mg. of the active ingredient for multiple dosage or in 10 ampules for single dosage.

What is claimed is:

1. A compound of the formula

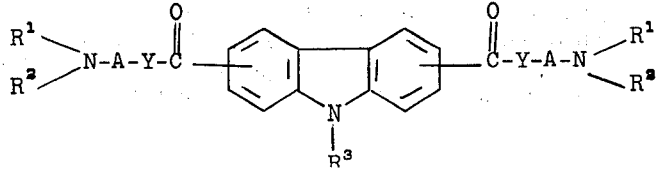

wherein:
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent Y and amino nitrogen by an alkylene chain of at least 2 carbon atoms;
C. each Y is oxygen, or N-R wherein R is hydrogen, methyl or ethyl; and
D. $R^3$ is hydrogen or (lower) primary or secondary alkyl, or an acid addition salt thereof.

2. A compound of claim 1 wherein: each A is alkylene of 3 to 6 carbon atoms; and each of the

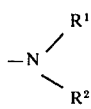

groups is a tertiary amino group selected from di(lower)alkylamino, dialkenylamino or each set of $R^1$ and $R^2$ together with the nitrogen to which they are attached is pyrrolidino, piperidino, N-(lower)alkylpiperazino or morpholino.

3. A compound of claim 1 wherein the side chains

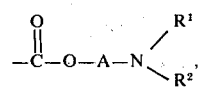

are in the 1,8- or 2,6- or 3,6-positions of the carbazole ring.

4. A compound of the formula

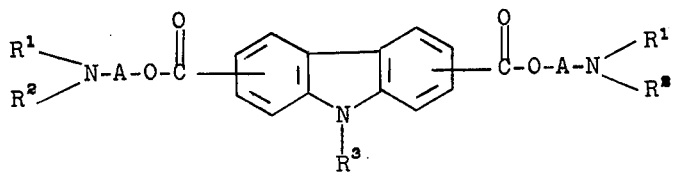

wherein:
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent O and amino nitrogen by an alkylene chain of at least 2 carbon atoms;
C. $R^3$ is hydrogen or (lower) primary or secondary alkyl; or a pharmaceutically acceptable acid addition salt thereof.

5. A compound of claim 4 wherein each A is alkylene of 3 to 6 carbon atoms and each of the

groups is a tertiary amino group selected from di(lower)alkylamino, dialkenylamino or each set of $R^1$ and $R^2$ together with the nitrogen to which they are attached is pyrrolidino, piperidino, N-(lower)alkylpiperazino or morpholino.

6. A compound of claim 5 wherein the side chains,

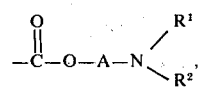

are in the 3- and 6-positions of the carbazole ring.

7. A compound of claim 6 wherein $R^3$ is (lower) primary or secondary alkyl.

8. A compound of claim 7 wherein each of $R^1$ and $R^2$ is (lower)alkyl.

9. A compound of the formula

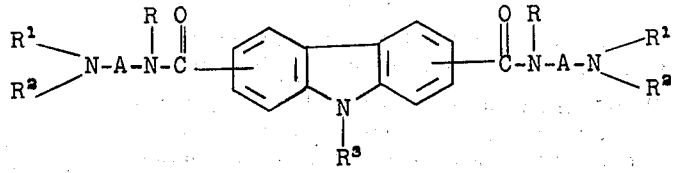

wherein:
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent amide nitrogen and amino nitrogen by an alkylene chain of at least 2 carbon atoms;
C. each R is hydrogen, methyl or ethyl; and
D. $R^3$ is hydrogen or (lower) primary or secondary alkyl; or a pharmaceutically acceptable acid addition salt thereof.

10. A compound of claim 9 wherein: each R is hydrogen; each A is alkylene of 3 to 6 carbon atoms; and each of the

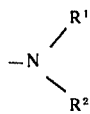

groups is a tertiary amino group selected from di(lower)alkylamino, dialkenylamino or each set of $R^1$ and $R^2$ together with the nitrogen to which they are attached is pyrrolidino, piperidino, N-(lower)alkylpiperazino or morpholino.

11. A compound of claim 10 wherein the side chains,

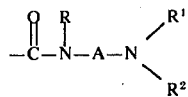

are in the 3- and 6-positions of the carbazole ring.

12. A compound of claim 11 wherein $R^3$ is (lower) primary or secondary alkyl.

13. A compound of claim 12 wherein each of $R^1$ and $R^2$ is (lower)alkyl.

14. Bis(3-diethylaminopropyl) 9-ethylcarbazole-3,6-dicarboxylate or a pharmaceutically acceptable acid addition salt thereof.

15. Bis(3-diethylaminopropyl) carbazole-3,6-dicarboxylate or a pharmaceutically acceptable acid addition salt thereof.

* * * * *